United States Patent

Mori et al.

[11] Patent Number: 6,113,887
[45] Date of Patent: Sep. 5, 2000

[54] TOOTHPASTE COMPOSITION

[75] Inventors: Shigeki Mori; Takako Nakajima, both of Takatsuki, Japan

[73] Assignee: Sunstar Kabushiki Kaisha, Osaka, Japan

[21] Appl. No.: 08/170,839

[22] Filed: Dec. 21, 1993

[30] Foreign Application Priority Data

Dec. 21, 1992 [JP] Japan ..................................... 4-340076
Nov. 8, 1993 [JP] Japan ..................................... 5-278191

[51] Int. Cl.$^7$ ....................................... A61K 7/16
[52] U.S. Cl. ................................. 424/54; 424/49
[58] Field of Search ......................... 424/54, 49

[56] References Cited

U.S. PATENT DOCUMENTS 3,472,840  10/1969  Stone et al. ................................ 424/54
5,176,901   1/1993  Gallopo et al. ........................... 424/54

FOREIGN PATENT DOCUMENTS 0368130  5/1990  European Pat. Off. .
0422803  4/1991  European Pat. Off. .
601116   1/1985  Japan .

Primary Examiner—Keith D. MacMillan
Attorney, Agent, or Firm—Foley & Lardner

[57] ABSTRACT

There is disclosed a toothpaste composition containing: (1) a water-soluble bactericide selected from the group consisting of pyridinium compounds, quaternary ammonium compounds and biguanide compounds in an amount of 0.001% to 5.0% by weight, based on the total weight of the composition; (2) a cationically-modified hydroxyethylcellulose having an average molecular weight of 1,000,000 or higher in the hydroxyethylcellulose portion thereof and having a cationization degree of 0.05 to 0.5 mol/glucose in an amount of 0.5% to 5.0% by weight, based on the total weight of the composition; (3) a surfactant selected from the group consisting of polyoxyethylene polyoxypropylene block copolymers and alkylolamide compounds in an amount of 0.5% to 13% by weight, based on the total weight of the composition; and (4) a polishing agent of the non-silica type in an amount of 5% to 50% by weight, based on the total weight of the composition.

5 Claims, No Drawings

TOOTHPASTE COMPOSITION

FIELD OF THE INVENTION

The present invention relates to a toothpaste composition, and more particularly, it relates to an anti-plaque toothpaste composition having stable bactericidal activity and excellent rheological properties.

BACKGROUND OF THE INVENTION

Water-soluble pyridinium compounds, quaternary ammonium compounds and biguanide compounds are effective cationic bactericides for inhibition of plaque formation, and there have hitherto been made a proposition that these bactericides are blended in toothpaste compositions. When these compounds are mixed with anionic ingredients such as thickening agents or surfactants in toothpaste compositions, they may cause electric reaction to deteriorate their bactericidal activity because of their cationic properties. To prevent such an electric inactivation of bactericidal activity, there is proposed a combination of cationic bactericides and nonionic thickening agents or cationic polymers (see, e.g., JP-A 2-223511, JP-A 3-127718 and U.S. Pat. No. 5,176,901). However, although the bactericidal activity of the cationic bactericides is stabilized in these compositions, the compositions have poor paste-shape retention and poor rheological properties in the sense of use.

To obtain a toothpaste composition having good shape retention, there has been made a proposition that a cationic polymer is blended in the composition. For example, a cationic polymer is combined with silica to cause flocculation between both substances, so that thickening properties are improved to form a gel. However, the gel stability is readily deteriorated with time, such as solid-liquid separation, and silica has silanol groups which can absorb any cationic bactericide and thereby inactivate its bacteriocidal activity.

SUMMARY OF THE INVENTION

Under these circumstances, the present inventors have intensively studied to provide a toothpaste composition having stable bactericidal activity and excellent rheological properties. As the result, they have found that a certain cationically-modified hydroxyethylcellulose (hereinafter referred to as cationically-modified HEC) having a particular molecular weight and having a particular cationization degree can give thickening properties without causing any flocculation with silica and it is, therefore, possible to obtain a toothpaste composition having stable bactericidal activity and excellent rheological properties by blending such a cationically-modified HEC with a water-soluble bactericide selected from pyridinium compounds, quaternary ammonium compounds and biguanide compounds, thereby completing the present invention.

Thus, the present invention provides an anti-plaque toothpaste composition comprising: (1) a water-soluble bactericide selected from the group consisting of pyridinium compounds, quaternary ammonium compounds and biguanide compounds in an amount of 0.001% to 5.0% by weight, based on the total weight of the composition; (2) a cationically-modified hydroxyethylcellulose having an average molecular weight of 1,000,000 or higher in the hydroxyethylcellulose portion thereof and having a cationization degree of 0.05 to 0.5 mol/glucose in an amount of 0.5% to 5.0% by weight, based on the total weight of the composition; (3) a surfactant selected from the group consisting of polyoxyethylene polyoxypropylene block copolymers and alkylolamide compounds in an amount of 0.5% to 13% by weight, based on the total weight of the composition; and (4) a polishing agent of the non-silica type in an amount of 5% to 50% by weight, based on the total weight of the composition. The toothpaste composition of the present invention can exhibit stable bactericidal activity and excellent rheological properties such as paste-shape retention.

DETAILED DESCRIPTION OF THE INVENTION

The toothpaste composition of the present invention contains a water-soluble pyridinium compound, quaternary ammonium compound or biguanide compound as a bactericide. The pyridinium compound which can be used in the present invention is not particularly limited, so long as it is soluble in water. Preferred is cetylpyridinium chloride. The quaternary ammonium compound which can be used in the present invention is also not particularly limited, so long as it is soluble in water. Preferred are benzethonium chloride and benzalkonium chloride. The biguanide compound which can be used in the present invention is also not particularly limited, so long as it is soluble in water. Preferred are mono-biguanide compounds such as p-chlorobenzylbiguanide; bisguanide compounds such as chlorhexidine and alexidine; polybiguanide compounds such as polyhexamethylenebiguanide hydrochloride. More preferred are salts of chlorhexidine.

These water-soluble bactericides may be used alone or in combination. The amount of water-soluble bactericide to be used is usually in the range of 0.001% to 5.0% by weight, preferably 0.01% to 0.5% by weight, based on the total weight of the composition.

The cationically-modified HECs are cationic polymers obtainable, for example, by addition of 3-chloro-2-hydroxypropyltrimethylammonium chloride to hydroxyethylcellulose. The cationically-modified HEC which can be used in the present invention has an average molecular weight of about 1,000,000 or higher, preferably 1,000,000 to 3,000,000, and more preferably 1,500,000 to 2,700,000, in the hydroxyethylcellulose portion thereof and has a cationization degree (i.e., average moles of cationic groups added to each of the glucose units constituting the cellulose portion thereof) of 0.05 to 0.5 mol/glucose. The amount of cationically-modified HEC to be used is usually in the range of 0.5% to 5.0% by weight, preferably 1.0% to 2.0% by weight, based on the total weight of the composition. The use of cationically-modified HEC makes it unnecessary to use any other thickening agent.

The polyoxyethylene-polyoxypropylene block copolymers which can be used in the present invention are conventional nonionic surfactants which are commercially available, for example, under the trade name "PLURONIC" from BASF Corporation in U.S.A. The alkylolamide compounds are also conventional nonionic surfactants of the general formula:

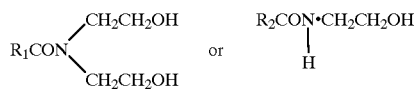

wherein $R_1$ and $R_2$ are independently $C_8$ to $C_{18}$ alkyl. Examples of the alkylolamide are lauric acid monoethanolamide, lauric acid diethanolamide, coconut oil fatty acid monoethanolamide and coconut oil fatty acid diethanolamide. The alkylolamide is commercially available, for example, under the trade name "TOHOL" from Toho Kagaku Kogyo, Co., Ltd.

The surfactant may be blended in an amount of 0.5% to 13% by weight, preferably 1.0% to 10% by weight, based on the total weight of the composition.

The polishing agent of the non-silica type which can be used in the present invention is selected so as to meet the conditions that it has no silanol groups and does not cause any absorption of cationic bactericides and their inactivation associated therewith. Examples of the polishing agent are calcium secondary phosphate dihydrate and anhydride, calcium primary phosphate, calcium tertiary phosphate, calcium carbonate, calcium pyrophosphate, aluminum hydroxide, alumina, insoluble sodium metaphosphate, magnesium tertiary phosphate, magnesium carbonate, calcium sulfate, polymethyl methacrylate and synthetic resins. These polishing agents may be used alone or in combination. The amount of polishing agent to be used is usually in the range of 5% to 50% by weight, preferably 10% to 40% by weight, based on the total weight of the composition.

The toothpaste composition of the present invention can be produced by any conventional method. Depending upon the type of toothpaste compositions, appropriate ingredients such as humecants, flavoring agents, sweeteners and other therapeutic agents can also be blended into the composition, so long as the effects of the present invention will not be deteriorated.

Examples of the humecant are sorbitol, glycerin, ethylene glycol, propylene glycol, 1,3-butylene glycol, polyethylene glycol, polypropylene glycol, xylitol, maltitol and lactitol. These wetting agents may be used alone or in combination. The amount of humecant to be used is usually in the range of 5% to 70% by weight, based on the total weight of the composition.

Examples of the flavoring agent are menthol, carvone, anethole, eugenol, methyl salicylate, limonene, cymene, n-decyl alcohol, citronellol, α-terpineol, methyl acetate, citronellyl acetate, methyl eugenol, cineole, linalool, ethyl linalool, vanillin, thymol, spearmint oil, peppermint oil, lemon oil, orange oil, sage oil, rosemary oil, cinnamon oil, pellira oil, gaultheria oil, clove oil and eucalyptus oil. These flavoring agents may be used alone or in combination. The amount of flavoring agent to be used is usually in the range of about 0.1% to 10% by weight, preferably about 0.5% to 5% by weight, based on the total weight of the composition.

Examples of the sweetener are saccharin sodium, Acesulfame K, stevioside, neo-hesperidyl dihydrochalcone, glycyrrhizin, perillartine, thaumatin, aspartylphenylalanine methyl ester and ρ-methoxycinnamic aldehyde. These sweeteners may be used alone or in combination. The amount of sweetener to be used is usually in the range of 0.01% to 1% by weight, preferably 0.05% to 0.5% by weight, based on the total weight of the composition.

Examples of the therapeutic agent are nonionic bactericides such as tricrosan; amphoteric bactericides such as dodecyldiaminoethylglycine; enzymes such as dextranase, amylase, protease, mutanase, lysozyme and lytic enzymes; monofluorophosphates of alkali metals, such as sodium monofluorophosphate and potassium monofluorophophate; fluorides such as sodium fluoride and stannous fluoride; tranexarnic acid and ε-aminocapric acid; aluminum chlorhydroxyl allantoin; dihydrocholesterol, glycyrrhizin salts, glycyrrhetic acid, glycerophosphate, chlorophyll, sodium chloride, caropeptide and water-soluble compounds of inorganic phosphoric acid. These therapeutic agents may be used alone or in combination.

The present invention will be further illustrated by way of the following examples and comparative examples, which are not to be construed to limit the scope thereof. Unless otherwise indicated, percents (%) are all by weight.

EXAMPLES 1 AND 4 AND COMPARATIVE EXAMPLES 1 TO 20

Various toothpaste compositions were prepared from the formulations as shown in Tables 1 and 2 according to the conventional procedures. Amounts in these tables are all in percent by weight.

The toothpaste compositions thus obtained were measured for their bactericidal activity and paste-shape retention by the following measurement method.

Bactericidal Activity Test

About six grams of each toothpaste composition was weighed out, and suspended in distilled water, followed by centrifugation, which afforded a supernatant. The supernatant thus obtained was diluted with distilled water into three kinds of dilutions each containing cetylpyridinium chloride or benzethonium chloride in a concentration of 0.0001%, 0.0002% or 0.0004%.

In another step, cetylpyridinium chloride and benzethonium chloride were separately dissolved in distilled water to have a concentration of 0.0001%, 0.0002% or 0.0004%. These six kinds of dilutions were used as standard solutions for measurements of the minimum bactericidal concentration (%) (hereinafter referred to as MBC). For chlorhexidine hydrochloride and chlorhexidine gluconate, the standard solutions for measurements of MBC were prepared in the same manner as described above, except that the concentration was set to be 0.0125%, 0.025% or 0.05%.

To 10 ml of each prepared sample, 0.1 ml of suspension containing Streptococcus mutans at a proportion of $10^8$ to $10^9$ CFU/ml was added. The mixture was allowed to cause bactericidal reaction in water bath at 37° C. for 15 minutes. After the reaction, a loopful of the sample mixture was plated on a trypticase soy agar (TSA) plate containing 0.5% polyoxyethylene monoolate and 0.07% lecithin, and incubated at 37° C. under anaerobic conditions ($N_2/H_2/CO_2$=85/10/5) for 2 days, followed by measurements of MBC.

The standard MBC was 0.0002% for cetylpyridinium chloride and benzethonium chloride, and 0.025% for chlorhexidine hydrochloride and chlorhexidine gluconate.

The test samples were evaluated for MBC according to the following criteria:

A: MBC of the test sample is not greater than the standard MBC;

B: MBC of the test sample is greater than the standard MBC.

Paste-shape Retention Measurement

The paste-shape retention was measured by the rack test (using a rack made of parallel wires successively fixed with a spacing of 1, 4, 8, 10, 13, 16, 19, 22, 25, 28, 32 and 34 mm). On the rack, each toothpaste composition was squeezed from a laminate tube with a cap having a pinhole of 1 mm in diameter, and the paste-shape retention was measured by determining which spacing the toothpaste composition was broken at after 30 seconds.

The test samples were evaluated for shape retention according to the following criteria:

A: broken at a rack spacing of 22 mm or wider;

B: broken at a rack spacing of narrower than 22 mm.

The results are shown in Tables 1 and 2.

As can be seen from Tables 1 and 2, when cationic or nonionic thickening agents are used, the bactericidal activity of cetylpyridinium chloride, benzethonium chloride, chlorhexidine hydrochloride or chlorhexidine gluconate were maintained stable. Further, only cationically-modified HEC gave satisfactory paste-shape retention. When alkylolamide compounds were used as a surfactant in place of polyoxyethylene polyoxypropylene block copolymers, similar results were obtained.

TABLE 1

|  | Examples | | Comparative Examples | | | | | | | | | |
|---|---|---|---|---|---|---|---|---|---|---|---|---|
| Ingredients | 1 | 2 | 1 | 2 | 3 | 4 | 5 | 6 | 7 | 8 | 9 | 10 |
| Water-soluble pyridinium compound: | | | | | | | | | | | | |
| Cetylpyridinium chloride | 0.2 | — | 0.2 | 0.2 | 0.2 | 0.2 | 0.2 | — | — | — | — | — |
| Water-soluble quaternary ammonium compound: | | | | | | | | | | | | |
| Benzethonium chloride | — | 0.2 | — | — | — | — | — | 0.2 | 0.2 | 0.2 | 0.2 | 0.2 |
| Cationic thickening agent | | | | | | | | | | | | |
| Cationically-modified HEC (HEC average molecular weight: 2,000,000; cationization degree: 0.20) | 1.5 | 1.5 | — | — | — | — | — | — | — | — | — | — |
| Dimethyldiallylammonium chloride polymer | — | 1.5 | — | — | — | — | — | 1.5 | — | — | — | — |
| Cationically-modified guar gum | — | — | — | 1.5 | — | — | — | — | 1.5 | — | — | — |
| Cationically-modified locust bean gum | — | — | — | — | 1.5 | — | — | — | — | 1.5 | — | — |
| Nonionic thickening agent: | | | | | | | | | | | | |
| Hydroxyethyl cellulose | — | — | — | — | — | 1.5 | — | — | — | — | 1.5 | — |
| Anionic thickening agent: | | | | | | | | | | | | |
| Sodium carboxymethyl cellulose | — | — | — | — | — | — | 1.5 | — | — | — | — | 1.5 |
| Polyoxyethylene (194)* polyoxypropylene glycol (39)* | 8.0 | 8.0 | 8.0 | 8.0 | 8.0 | 8.0 | 8.0 | 8.0 | 8.0 | 8.0 | 8.0 | 8.0 |
| Calcium hydrogenphosphate | 30.0 | 30.0 | 30.0 | 30.0 | 30.0 | 30.0 | 30.0 | 30.0 | 30.0 | 30.0 | 30.0 | 30.0 |
| Glycerol | 20.0 | 20.0 | 20.0 | 20.0 | 20.0 | 20.0 | 20.0 | 20.0 | 20.0 | 20.0 | 20.0 | 20.0 |
| flavor | 1.0 | 1.0 | 1.0 | 1.0 | 1.0 | 1.0 | 1.0 | 1.0 | 1.0 | 1.0 | 1.0 | 1.0 |
| Saccharin sodium | 0.1 | 0.1 | 0.1 | 0.1 | 0.1 | 0.1 | 0.1 | 0.1 | 0.1 | 0.1 | 0.1 | 0.1 |
| Purified water | Balance | Balance | Balance | Balance | Balance | Balance | Balance | Balance | Balance | Balance | Balance | Balance |
| Total | 100.0 | 100.0 | 100.0 | 100.0 | 100.0 | 100.0 | 100.0 | 100.0 | 100.0 | 100.0 | 100.0 | 100.0 |
| Bacteriocidal activity | A | A | A | A | A | A | B | A | A | A | A | B |
| Paste-shape retention | A | A | B | B | B | B | A | B | B | B | B | A |

*Each numeral in parentheses means an average polymerization degree in the corresponding portion.

TABLE 2

|  | Examples | | Comparative Examples | | | | | | | | | |
|---|---|---|---|---|---|---|---|---|---|---|---|---|
| Ingredients | 3 | 4 | 11 | 12 | 13 | 14 | 15 | 16 | 17 | 18 | 19 | 20 |
| Biguanide compound: | | | | | | | | | | | | |
| Chlorhexidine hydrochloride | 0.2 | — | 0.2 | 0.2 | 0.2 | 0.2 | 0.2 | — | — | — | — | — |
| Chlorhexidine gluconate | — | 0.2 | — | — | — | — | — | 0.2 | 0.2 | 0.2 | 0.2 | 0.2 |
| Cationic thickening agent: | | | | | | | | | | | | |
| Cationically-modified HEC (HEC average molecular weight: 2,000,000; cationization degree: 0.20) | 1.5 | 1.5 | — | — | — | — | — | — | — | — | — | — |
| Dimethyldiallylammonium chloride polymer | — | — | 1.5 | — | — | — | — | 1.5 | — | — | — | — |
| Cationically-modified guar gum | — | — | — | 1.5 | — | — | — | — | 1.5 | — | — | — |
| Cationically-modified locust bean gum | — | — | — | — | 1.5 | — | — | — | — | 1.5 | — | — |
| Nonionic thickening agent: | | | | | | | | | | | | |
| Hydroxyethyl celllose | — | — | — | — | — | 1.5 | — | — | — | — | 1.5 | — |

TABLE 2-continued

| | Examples | | Comparative Examples | | | | | | | | | |
|---|---|---|---|---|---|---|---|---|---|---|---|---|
| Ingredients | 3 | 4 | 11 | 12 | 13 | 14 | 15 | 16 | 17 | 18 | 19 | 20 |
| Anionic thickening agent: | | | | | | | | | | | | |
| Sodium carboxymethyl cellulose | — | — | — | — | — | — | 1.5 | — | — | — | — | 1.5 |
| Polyoxyethylene (194)* polyoxypropylene glycol (39)* | 8.0 | 8.0 | 8.0 | 8.0 | 8.0 | 8.0 | 8.0 | 8.0 | 8.0 | 8.0 | 8.0 | 8.0 |
| Calcium hydrogenphosphate | 30.0 | 30.0 | 30.0 | 30.0 | 30.0 | 30.0 | 30.0 | 30.0 | 30.0 | 30.0 | 30.0 | 30.0 |
| Glycerol | 20.0 | 20.0 | 20.0 | 20.0 | 20.0 | 20.0 | 20.0 | 20.0 | 20.0 | 20.0 | 20.0 | 20.0 |
| Flavor | 1.0 | 1.0 | 1.0 | 1.0 | 1.0 | 1.0 | 1.0 | 1.0 | 1.0 | 1.0 | 1.0 | 1.0 |
| Saccharin sodium | 0.1 | 0.1 | 0.1 | 0.1 | 0.1 | 0.1 | 0.1 | 0.1 | 0.1 | 0.1 | 0.1 | 0.1 |
| Purified water | Balance | Balance | Balance | Balance | Balance | Balance | Balance | Balance | Balance | Balance | Balance | Balance |
| Total | 100.0 | 100.0 | 100.0 | 100.0 | 100.0 | 100.0 | 100.0 | 100.0 | 100.0 | 100.0 | 100.0 | 100.0 |
| Bacteriocidal activity | A | A | A | A | A | A | B | A | A | A | A | B |
| Paste-shape retention | A | A | B | B | B | B | A | B | B | B | B | A |

*Each numeral in parentheses means an average polymerization degree in the corresponding portion.

EXAMPLES 5 TO 12 AND COMPARATIVE EXAMPLES 21 TO 26

Various toothpaste compositions were prepared from the formulations as shown in Tables 3 and 4 according to the conventional procedures. Amounts in these tables are all in percent by weight.

As can be seen from Tables 3 and 4, the blending of cationically-modified HEC having an average molecular weight of 1,000,000 or higher in the HEC portion thereof and having a cationization degree of 0.05 to 0.50 gave toothpaste compositions with good shape retention. Similar results were obtained, when benzethonium chloride was used in place of cetylpyridinium chloride, or when chlorhexidine hydrochloride was used in place of chlorhexidine gluconate, or when an alkylolamide compound was used as a surfactant in place of a polyoxyethylene polyoxypropylene block copolymer.

TABLE 3

| | | Examples | | | | Comparative Examples | | |
|---|---|---|---|---|---|---|---|---|
| Ingredients | | 5 | 6 | 7 | 8 | 21 | 22 | 23 |
| Cationically-modified HEC | | | | | | | | |
| HEC average molecular weight | Cationization (mol/glucose) | | | | | | | |
| 1,000,000 | 0.20 | 1.5 | — | — | — | — | — | — |
| 3,000,000 | 0.20 | — | 1.5 | — | — | — | — | — |
| 2,000,000 | 0.05 | — | — | 1.5 | — | — | — | — |
| 2,000,000 | 0.50 | — | — | — | 1.5 | — | — | — |
| 2,000,000 | 0.01 | — | — | — | — | 1.5 | — | — |
| 2,000,000 | 0.60 | — | — | — | — | — | 1.5 | — |
| 500,000 | 0.20 | — | — | — | — | — | — | 1.5 |
| Cetylpyridinium chloride | | 0.2 | 0.2 | 0.2 | 0.2 | 0.2 | 0.2 | 0.2 |
| Polyoxyethylene (194)* polyoxypropylene glycol (39)* | | 8.0 | 8.0 | 8.0 | 8.0 | 8.0 | 8.0 | 8.0 |
| Calcium hydrogenphosphate | | 30.0 | 30.0 | 30.0 | 30.0 | 30.0 | 30.0 | 30.0 |
| Glycerol | | 20.0 | 20.0 | 20.0 | 20.0 | 20.0 | 20.0 | 20.0 |
| Flavor | | 1.0 | 1.0 | 1.0 | 1.0 | 1.0 | 1.0 | 1.0 |
| Saccharin sodium | | 0.1 | 0.1 | 0.1 | 0.1 | 0.1 | 0.1 | 0.1 |
| Purified water | | Balance | Balance | Balance | Balance | Balance | Balance | Balance |
| Total | | 100.0 | 100.0 | 100.0 | 100.0 | 100.0 | 100.0 | 100.0 |
| Bacteriocidal activity | | A | A | A | A | A | A | A |
| Paste-shape retention | | A | A | A | A | B | B | B |

*Each numeral in parentheses means an average polymerization degree in the corresponding portion.

TABLE 4

|  |  | Examples | | | | Comparative Examples | | |
| --- | --- | --- | --- | --- | --- | --- | --- | --- |
| Ingredients | | 9 | 10 | 11 | 12 | 24 | 25 | 26 |
| Cationically-modified HEC | | | | | | | | |
| HEC average molecular weight | Cationization (mol/glucose) | | | | | | | |
| 1,000,000 | 0.20 | 1.5 | — | — | — | — | — | — |
| 3,000,000 | 0.20 | — | 1.5 | — | — | — | — | — |
| 2,000,000 | 0.05 | — | — | 1.5 | — | — | — | — |
| 2,000,000 | 0.50 | — | — | — | 1.5 | — | — | — |
| 2,000,000 | 0.01 | — | — | — | — | 1.5 | — | — |
| 2,000,000 | 0.60 | — | — | — | — | — | 1.5 | — |
| 500,000 | 0.20 | — | — | — | — | — | — | 1.5 |
| Chlorhexidine gluconate | | 0.2 | 0.2 | 0.2 | 0.2 | 0.2 | 0.2 | 0.2 |
| Polyoxyethylene (194)* polyoxypropylene glycol (39)* | | 8.0 | 8.0 | 8.0 | 8.0 | 8.0 | 8.0 | 8.0 |
| Calcium hydrogenphosphate | | 30.0 | 30.0 | 30.0 | 30.0 | 30.0 | 30.0 | 30.0 |
| Glycerol | | 20.0 | 20.0 | 20.0 | 20.0 | 20.0 | 20.0 | 20.0 |
| Flavor | | 1.0 | 1.0 | 1.0 | 1.0 | 1.0 | 1.0 | 1.0 |
| Saccharin sodium | | 0.1 | 0.1 | 0.1 | 0.1 | 0.1 | 0.1 | 0.1 |
| Purified water | | Balance | Balance | Balance | Balance | Balance | Balance | Balance |
| Total | | 100.0 | 100.0 | 100.0 | 100.0 | 100.0 | 100.0 | 100.0 |
| Bacteriocidal activity | | A | A | A | A | A | A | A |
| Paste-shape retention | | A | A | A | A | B | B | B |

*Each numeral in parentheses means an average polymerization degree in the corresponding portion.

EXAMPLE 13

A toothpaste composition was prepared from the following formulation according to the conventional procedures.

| Ingredients | Amounts (wt %) |
| --- | --- |
| Benzethonium chloride | 0.1 |
| Cationically-modified HEC (HEC average molecular weight: 2,200,000, cationization degree: 0.15) | 1.5 |
| Coconut oil fatty acid monoethanolamide | 2.0 |
| Aluminum hydroxide | 35.0 |
| Sorbitol | 35.0 |
| Sodium fluoride | 0.2 |
| Flavor | 1.0 |
| Saccharin sodium | 0.2 |
| Purified water | Balance |

The toothpaste composition of this example also exhibited good bactericidal activity and good paste-shape retention.

EXAMPLE 14

A toothpaste composition was prepared from the following formulation according to the conventional procedures.

| Ingredients | Amounts (wt %) |
| --- | --- |
| Cetylpyridinium chloride | 0.1 |
| Cationically-modified HEC (HEC molecular weight: 1,500,000, cationization degree: 0.20) | 2.0 |
| PLURONIC F-77 (average polymerization degree: ethylene oxide, 104; and propylene oxide, 35) | 6.0 |
| Polyethylene glycol 400 | 20.0 |
| Calcium carbonate | 25.0 |
| Mutanase | 0.5 |
| Flavor | 0.8 |
| Saccharin sodium | 0.1 |
| Purified water | Balance |

The toothpaste composition of this example also exhibited good bactericidal activity and good paste-shape retention.

EXAMPLE 15

A toothpaste composition was prepared from the following formulation according to the conventional procedures.

| Ingredients | Amounts (wt %) |
| --- | --- |
| Chlorhexidine gluconate | 0.1 |
| Cationically-modified HEC (HEC average molecular weight: 2,200,000, cationization degree: 0.15) | 1.5 |
| Coconut oil fatty acid monoethanolamide | 2.0 |
| Aluminum hydroxide | 35.0 |
| Sorbitol | 35.0 |
| Sodium fluoride | 0.2 |
| Flavor | 1.0 |
| Saccharin sodium | 0.2 |
| Purified water | Balance |

The toothpaste composition of this example also exhibited good bactericidal activity and good paste-shape retention.

EXAMPLE 16

A toothpaste composition was prepared from the following formulation according to the conventional procedures.

| Ingredients | Amounts (wt %) |
|---|---|
| Chlorhexidine hydrochloride | 0.1 |
| Cationically-modified HEC (HEC molecular weight: 1,500,000, cationization degree: 0.20) | 1.5 |
| PLURONIC F-77 (average polymerization degree: ethylene oxide, 104; and propylene oxide, 35) | 6.0 |
| Polypropylene glycol 400 | 20.0 |
| Calcium carbonate | 25.0 |
| Mutanase | 0.5 |
| Flavor | 1.0 |
| Saccharin sodium | 0.1 |
| Water | Balance |

The toothpaste composition of this example also exhibited good bactericidal activity and good paste-shape retention.

What is claimed is:

1. A toothpaste composition comprising:
   (1) a water-soluble bactericide selected from the group consisting of pyridinium compounds, quaternary ammonium compounds and biguanide compounds in an amount of 0.001% to 5.0% by weight, based on the total weight of the composition;
   (2) a cationically-modified hydroxyethylcellulose having an average molecular weight of 1,000,000 or higher in the hydroxyethylcellulose portion thereof and having a cationization degree of 0.05 to 0.5 mol/glucose in an amount of 0.5% to 5.0% by weight, based on the total weight of the composition;
   (3) a surfactant selected from the group consisting of polyoxyethylene polyoxypropylene block copolymers and alkylolamide compounds in an amount of 0.5% to 13% by weight, based on the total weight of the composition; and
   (4) a polishing agent of the non-silica type in an amount of 5% to 50% by weight, based on the total weight of the composition.

2. A toothpaste composition according to claim 1, wherein the water-soluble bactericide is cetylpyridinium chloride.

3. A toothpaste composition according to claim 1, wherein the water-soluble bactericide is benzethonium chloride or benzalkonium chloride.

4. A toothpaste composition according to claim 1, wherein the water-soluble bactericide is a salt of chlorhexidine.

5. A toothpaste composition according to claim 1, wherein the cationically-modified hydroxyethylcellulose is hydroxyethylcellulose hydroxypropyltrimethyl-ammonium chloride ether.

* * * * *